United States Patent [19]

Mason, Jr. et al.

[11] 4,393,048
[45] Jul. 12, 1983

[54] PROTECTIVE GEL COMPOSITION FOR WOUNDS

[75] Inventors: Arthur D. Mason, Jr.; Avery A. Johnson, Jr., both of San Antonio; Harrel L. Walker, Sutherland Springs; Eleanor G. Bowler, San Antonio, all of Tex.; Charles R. Ritchey, Stillwater, Okla.

[73] Assignee: The United States of America as represented by the Secretary of the Army, Washington, D.C.

[21] Appl. No.: 316,574

[22] Filed: Oct. 30, 1981

Related U.S. Application Data

[63] Continuation of Ser. No. 121,868, Feb. 15, 1980, abandoned.

[51] Int. Cl.³ .............................................. A61K 33/38
[52] U.S. Cl. .................................. 424/132; 424/228; 424/364; 424/DIG. 13
[58] Field of Search ............... 424/132, DIG. 13, 228

[56] References Cited

U.S. PATENT DOCUMENTS

| | | | |
|---|---|---|---|
| 2,338,416 | 1/1944 | Fales | 424/DIG. 13 X |
| 2,405,861 | 8/1946 | Tod | 252/316 |
| 2,845,381 | 7/1958 | Tindall | 424/DIG. 13 X |
| 3,639,575 | 2/1972 | Schmolka | 424/132 |
| 3,761,590 | 9/1973 | Fox | 424/DIG. 13 X |

OTHER PUBLICATIONS

Lachman et al.—The Theory & Practice of Industrial Pharmacy, 2nd ed. (1976), pp. 229-230.
Gooding et al.—Journal of the American Medical Assoc., (1942), p. 1059.

*Primary Examiner*—Leonard Schenkman
*Attorney, Agent, or Firm*—William G. Gapcynski; Werten F. W. Bellamy; John M. Petruncio

[57] ABSTRACT

Water soluble hydrogels of alkali metal alginate and glycerine have been found to be excellent wound dressings. The gels dry to an adherent, non-toxic pliable protective film which can be removed by water-washing when desired. The gels are also compatible with medicaments and hence can serve as vehicles or carriers for medicament application to wounds as well as a protective cover.

13 Claims, No Drawings

PROTECTIVE GEL COMPOSITION FOR WOUNDS

This is a continuation of application serial No. 121,868, filed Feb. 15, 1980, now abandoned.

BACKGROUND OF THE INVENTION

1. Field of the Invention

This invention relates to novel gel compositions and to their use in the protection of surface wounds. More particularly, the invention is directed to water-soluble gel compositions which dry to a pliable film which makes them especially suited for use as wound dressings.

2. Brief Description of the Prior Art

Gel preparations and protective films of various types are known and have been employed for the treatment of surface wounds. For example, U.S. Pat. No. 3,949,742 to B. Nowakowski, discloses a transparent medical dressing comprised of a laminate of a thin layer of non-porous segmented polyurethane cohesively secured to a thin layer of thrombogenic reticulated foam. The medical dressing is permeable to gases but impermeable to liquids and bacteria and performs as a snythetic film over skin wounds.

U.S. Pat. No. 3,880,158 to A. Gurney discloses a composition comprised of a mixture of non-elastomeric and elastomeric block polymers in a aerosol container which can be sprayed over a wound to form a fibrous bandage thereover.

U.S. Pat. No. 3,879,168 to K. J. Franklin discloses a surgical dressing made of partially soluble alginic material in the form of gauze or wool characterised by a pH of 4 to 7 and a calcium content of 2–6% by weight.

While previous attempts to formulate bandage compositions such as those described above may protect wounds satisfactorily, they are not without their shortcomings. In all cases, prior art bandage or wound-covering compositions are deficient in one or more of the characteristics desired in wound-covering compositions set out below under the Objects of the Invention.

OBJECTS OF THE INVENTION

It is an object of the invention to provide a composition suitable as a protective composition for wounds which compositions upon application air dry to a tightly adherent flexible film.

Another object of the invention is to provide a wound dressing content which when dry provides a transparent film that prevents bacteria from reaching the wound.

Yet another object of the invention is to provide a material which can be easily applied over wounds in gel form and dried into a water-soluble film which can be removed from the wound by simple water-washing.

A further object of the invention is to provide a cheap and stable composition which is compatible with medicaments and can therefore serve as a carrier or vehicle for medicament application to wounds.

An additional object is to provide a composition which can be applied as a film over a previously applied layer or layers of the same composition without first removing the deeper layers.

Another object is to provide a novel method for protecting and treating surface wounds.

SUMMARY OF THE INVENTION

These and other objects of the invention are obtained by a gel composition comprising a water-soluble hydrogel of an alkali metal alginate and glycerine. In one aspect of the invention, a medicament is dispersed throughout the water-soluble hydrogel.

In accordance with the method of the invention, wounds are protected by applying over the wound surface a coating of the novel gel compositions and drying the coating to a water-soluble, flexible film.

The gel compositions of the invention may be prepared by simply stirring in water, alkali metal alginate, glycerine and optionally at least one medicament until a gel is formed. The order of addition is not critical but it is preferred to first stir in the alkali metal alginate and then the glycerine. If a medicament is to be included, it is preferably added after solution of the alkali metal alginate and glycerine or alternatively, after the alkali metal alginate and glycerine have formed a gel. Any suitable stirring means can be used to form the gel but best results are obtained with a mechanical homogenizer. The preferred alkali metal alignate of the invention is sodium alginate.

The proportions of alkali metal alginate, glycerine and water may vary depending upon the properties of the materials used and the particular use to which the composition will be put but in all instances, the components will be employed in hydrogel-forming proportions. In general, the hydrogel comprises about 0.5 to 3% by weight alkali metal alginate, about 8 to 12% by weight glycerine and about 82 to 90% by weight water. Advantageously, the proportions of gel components are selected so as to form a hydrogel having a pH in the range of 6.8 to 7.2 since a pH in this range is found to provide storage stable compositions.

Medicaments which can be incorporated in the novel gels of the invention include for instance, biocidal agents such as antibiotics, and bactercides; chemotherapeutic agents; drugs and the like. The concentrations of medicaments in the composition when employed will vary depending upon the particular medicament employed but in all instances will be an amount effective for its intended purpose. In general, the amount of medicament in the compositions of the invention will range from about 0.01 to 10% by weight.

The gel compositions of the invention are easily manipulated jelly materials and can be applied to a body surface by brush, applicator or any other of a variety of means. The applied gel coating has been found to dry on exposure to air at ambient temperature and form a non-toxic, transparent, flexible and stretchable film which is tightly adherent to the body surface. Thus, the film is useful in the protection of wounds from infection by organisms in the environment and from further injury by external agents. Its ability to stretch and bend without tearing or disturbing adherence to the wound enables it to be used over joints of human and animal bodies.

A particularly advantageous characteristic of compositions of the invention resides in the fact that they are water-soluble. Hence, dried film-coatings of the compositions can be removed when desired by a simple water-wash. In addition, reapplication of the composition over a previously applied area can be made without removing underlying layers of the composition.

The transparency of the composition of the invention enables one to observe the wound underneath and thereby closely follow the healing progress.

The following examples are included to further illustrate the present invention.

EXAMPLE 1

12.5 Grams of sodium alginate is slowly added with constant stirring to 400 milliliters of water at room temperature. After the sodium aliginate has been added and has formed a thick solution, 50 milliliters of glycerine is stirred in. As an aid toward obtaining a homogeneous solution, the aqueous glycerine-sodium alginate solution is homogenized using a Virtis "45? homogenizer. A gel with a pH of 7.0 is obtained which is stable when kept in a tightly closed container.

EXAMPLE 2

Ten milliliters of an aqueous nitrate solution containing 0.13 grams of silver nitrate is added slowly with honogenization to 53 grams of the glycerine-sodium alginate gel of Example I.

EXAMPLE 3

Five (5) grams of sodium alginate is stirred into 200 milliliters of water after which 20 millileters of glycerine is stirred in. Following solution of the sodium alginate and glycerine, 2-5 grams of Sulfamylon (mafenide acetate) is stirred in and the resulting solution homogenized.

The following Example 4 illustrates the protection offered by the gel compositions of the invention.

EXAMPLE 4

Fifteen 200 gm, male, Holtzman rats were burned over 20% of total body surface by 10 second exposure to 100° C. water. Nine animals were selected at random for application of the gel of Example I; six were not treated. After 24 hours, each burn wound was seeded with approximately $10^8$ colony forming units of Pseudomonas aeruginosa, ISR strain 8-28-3 (63); this dose was applied to the gel surface in the treated animal and to the burn surface in the untreated animals. The animals were then observed for 30 days, with daily reapplication of the gel to the burn wounds of the treated animals for the first 10 days of the observation period. Results were as shown in the following table.

| GROUP | POSTBURN DAY OF DEATH | NO. DEATHS | NO. ANIMALS |
| --- | --- | --- | --- |
| Treated | 17 | 1 | 9 |
| Control | 9,9,10,11,14 | 5 | 6 |

We claim:

1. A gel composition, having use as a wound dressing, comprising a water-soluble hydrogel consisting essentially of about 0.5 to 3% by weight of alkali metal alginate, about 8 to 12% by weight glycerine and about 82 to 90% by weight water wherein said hydrogel has a pH in the range of 6.8 to 7.2 and which upon drying forms a flexible, stretchable, transparent water-soluble protective film, nontoxic and adherent to a wound surface to which said gel composition is applied for protection.

2. A gel composition according to claim 1 wherein the alkali metal alginate is sodium alginate.

3. A gel composition according to claim 1 further comprising a medicament dispersed therein in an amount therapeutically effective as a wound dressing.

4. A gel composition according to claim 3 wherein the medicament is silver nitrate.

5. A gel composition according to claim 3 wherein the medicament is a sulfa drug.

6. A gel composition according to claim 3 wherein the medicament is an antibiotic.

7. A gel composition according to claim 3 wherein the medicament is a chemotherapeutic agent.

8. A gel composition according to claim 3 wherein the amount of medicament is in the range of from about 0.01% to about 10% by weight of the gel composition.

9. A gel composition according to claim 5 wherein the medicament is mafenide acetate.

10. A method for protecting wounds which comprises applying over a wound surface a coating of a gel composition comprising a water-soluble hydrogel consisting essentially of about 0.5 to 3% by weight alkali metal alginate, about 8 to 12% by weight glycerine and about 82 to 90% by weight water wherein said hydrogel has a pH in the range of 6.8 to 7.2 and allowing the coating to dry to a water-soluble, flexible, stretchable, transparent, protective film, non-toxic and adherent to said wound surface.

11. A method according to claim 10 wherein the alkali metal alginate is sodium alginate.

12. A method according to claim 10 wherein the gel composition comprises a medicament in an amount therapeutically effective as a wound dressing.

13. A method according to claim 10 wherein the wound is a burn wound.

* * * * *